United States Patent
Fern

(10) Patent No.: US 9,770,308 B2
(45) Date of Patent: Sep. 26, 2017

(54) AUTOMATIC LUBRICANT DISPENSER

(75) Inventor: Steven J. Fern, Wellington, FL (US)

(73) Assignee: Fern Innovations IP, LLC, Loxahatchee, FL (US)

(*) Notice: Subject to any disclaimer, the term of this patent is extended or adjusted under 35 U.S.C. 154(b) by 1263 days.

(21) Appl. No.: 13/106,480

(22) Filed: May 12, 2011

(65) Prior Publication Data

US 2011/0303695 A1 Dec. 15, 2011

Related U.S. Application Data

(60) Provisional application No. 61/353,301, filed on Jun. 10, 2010.

(51) Int. Cl.
| | | |
|---|---|---|
| A47K 5/12 | (2006.01) |
| A61B 90/80 | (2016.01) |
| A61B 17/225 | (2006.01) |
| A61B 17/00 | (2006.01) |

(52) U.S. Cl.
CPC ............ A61B 90/80 (2016.02); A47K 5/12 (2013.01); *A61B 2017/00889* (2013.01); *A61B 2017/2253* (2013.01)

(58) Field of Classification Search
CPC A47K 5/12; A61B 90/80; A61B 2017/00889; A61B 2017/2253
USPC ............................ 222/52, 63, 108, 333, 325
See application file for complete search history.

(56) References Cited

U.S. PATENT DOCUMENTS

| | | |
|---|---|---|
| 1,754,259 A | 4/1930 | Brown |
| 3,952,918 A * | 4/1976 | Poitras et al. ............. 222/82 |
| 4,154,375 A | 5/1979 | Bippus |
| 4,699,250 A | 10/1987 | Hiestand |
| 4,917,265 A | 4/1990 | Chiang |
| 4,921,131 A * | 5/1990 | Binderbauer et al. ......... 222/52 |
| 4,921,150 A * | 5/1990 | Lagergren ............ A47K 5/1215 137/624.11 |
| 4,946,070 A | 8/1990 | Albert |
| 4,967,935 A | 11/1990 | Celest |
| 5,105,992 A | 4/1992 | Fender |
| 5,409,084 A | 4/1995 | Graf |
| 5,477,984 A | 12/1995 | Sayama |
| 5,490,613 A | 2/1996 | Taylor |
| 5,695,091 A | 12/1997 | Winings |
| 5,700,991 A | 12/1997 | Osbern |
| 5,836,482 A | 11/1998 | Ophardt |
| 6,149,037 A | 11/2000 | Berrend |
| 6,161,726 A | 12/2000 | Parsons |

(Continued)

FOREIGN PATENT DOCUMENTS

| | | |
|---|---|---|
| EP | 0468062 | 1/1992 |
| WO | 2009088929 | 7/2009 |

OTHER PUBLICATIONS

Amazon: <<http://dispenser.2beblog.com>>, last visited on May 3, 2010.

(Continued)

*Primary Examiner* — Patrick M Buechner
(74) *Attorney, Agent, or Firm* — Cuenot, Forsythe & Kim, LLC; Stanley A. Kim

(57) ABSTRACT

A device for automatically dispensing lubricating gel for medical procedures that reduces the chance of cross-contamination between patients by use of a shape that prevent accidental contact with the dispenser, anti-microbial materials, and a dispensing valve protection device.

19 Claims, 2 Drawing Sheets

(56) References Cited

U.S. PATENT DOCUMENTS

| | | |
|---|---|---|
| 6,202,893 B1 | 3/2001 | Rufini |
| 6,209,751 B1 | 4/2001 | Goodin |
| 6,279,777 B1 | 8/2001 | Goodin |
| 6,311,864 B1 | 11/2001 | Land |
| 6,311,868 B1 | 11/2001 | Krietmeier |
| 6,390,329 B1 | 5/2002 | Maddox |
| 6,415,957 B1 | 7/2002 | Michaels |
| 6,431,189 B1 | 8/2002 | Deibert |
| 6,467,651 B1 | 10/2002 | Muderlak |
| 6,698,616 B2 | 3/2004 | Hidle |
| 6,755,325 B2 | 6/2004 | Haase |
| 6,830,164 B2 | 12/2004 | Michaels |
| 7,527,178 B2 | 5/2009 | Lewis |
| 8,678,244 B2 * | 3/2014 | Yang .................... A47K 5/1202 222/321.9 |
| 2002/0125271 A1 | 9/2002 | Zeitlin |
| 2003/0071066 A1* | 4/2003 | Nowak et al. ............. 222/181.1 |
| 2004/0155068 A1 | 8/2004 | Weigand |
| 2004/0226962 A1 | 11/2004 | Mazursky |
| 2006/0173405 A1 | 8/2006 | Haithcock |
| 2008/0185399 A1 | 8/2008 | Yang |
| 2009/0048706 A1* | 2/2009 | DeLine ........................ 700/231 |
| 2009/0101671 A1 | 4/2009 | Cittadino |
| 2009/0140004 A1* | 6/2009 | Scorgie ............................ 222/52 |
| 2009/0266842 A1 | 10/2009 | Snodgrass |
| 2009/0294471 A1 | 12/2009 | Paige |
| 2010/0084486 A1 | 4/2010 | Kim |
| 2011/0011886 A1* | 1/2011 | Zaima et al. ..................... 222/1 |
| 2012/0111884 A1* | 5/2012 | Choi ....................... B05B 9/043 222/52 |
| 2012/0273519 A1* | 11/2012 | Marshall .................. B67D 7/04 222/52 |
| 2013/0134183 A1* | 5/2013 | Van Diepen ......... A47K 5/1217 222/52 |
| 2013/0140323 A1* | 6/2013 | Yun ...................... A47K 5/1215 222/1 |
| 2013/0206789 A1* | 8/2013 | Van Diepen ......... A47K 5/1217 222/52 |
| 2014/0197192 A1* | 7/2014 | Atkins ................. A47K 5/1217 222/23 |
| 2014/0253336 A1* | 9/2014 | Ophardt ............... A47K 5/1202 340/573.1 |
| 2014/0353335 A1* | 12/2014 | Van Diepen ......... A47K 5/1201 222/52 |
| 2016/0228897 A1* | 8/2016 | Buckalter ........... B05B 11/0002 |
| 2016/0346796 A1* | 12/2016 | Roberts ................. A45D 34/00 |

OTHER PUBLICATIONS

Medi-inn Ltd: <<http://www.medi-inn.com/geldisp.htm>>, last visited on May 3, 2010.

Discovery Medical, Inc.: <<http://www.discoverymedical.com/HandSanitizerstand.htm>>, last visited on May 3, 2010.

\* cited by examiner

AUTOMATIC LUBRICANT DISPENSER

CROSS-REFERENCE TO RELATED APPLICATIONS

The present application claims the priority of U.S. provisional patent application Ser. No. 61/353,301 filed on Jun. 10, 2010, which is incorporated herein be reference.

FIELD OF THE INVENTION

The invention relates generally to the fields of fluid handling and medicine. More particularly, the invention relates to methods and devices for dispensing lubricating gel in a clinical setting.

BACKGROUND

Lubricating jellies and other lubricants are used in a large variety of medical procedures such as ultrasound imaging and examination of orifices. In pelvic and rectal exams, lubricants increase patient comfort by reducing friction that can irritate delicate tissues. Lubricating jelly is typically supplied in large squeeze tubes or bottles, or in single-use packets. For the former, a health care provider will squeeze a suitable amount of the lubricant onto gloved fingers and then apply the lubricant to the patient. In cases where a health care provider performs multiple examinations in a day (e.g., an obstetrician/gynecologist), use of squeeze tubes or bottles can create a significant risk of cross-contamination—i.e., bodily fluids or tissues from one patient are inadvertently transferred to another patient. Although the health care provider will change gloves between each patient, if the provider handles the tube or bottle with gloves used to examine a patient, there is a good chance that the tube or bottle will become contaminated with that patient's bodily fluids or tissue. Because few health care providers clean the lubricant tube or bottle between patients, the next use of the tube or bottle can transfer a previous patient's bodily fluids or tissue first onto the gloves of the health care provider and then onto the next patient.

Many practitioners are concerned about this issue and try to avoid contamination by using only one hand to contact the patient and the other hand to obtain lubricant from the squeeze tube or bottle. This of course can be quite awkward or even impossible to perform—especially in the case where two hands are required for the patient examination. As a result, lubricant containers are often contaminated—sometimes visibly so.

To overcome this problem, medical lubricants are also sold in single-use foil packets that are torn open for each use. Unfortunately, opening an individual packet of gel can be a messy and cumbersome process. And occasionally, a packet will cut the health care provider's protective glove—a dangerous and unsanitary situation for both the practitioner and the patient.

SUMMARY

The invention is based on the development of a device for dispensing of lubricating jelly that is specifically designed to reduce the potential of patient to patient cross contamination and to be easy to use by a health care provider. The device dispenses a predetermined volume of lubricant automatically when a health care provider's hand is placed near a sensor on the device, and importantly is shaped and sized to prevent a user's hand or glove from accidentally touching any component of the dispensing device. The device can be coated with suitable anti-microbial agents—particularly at those areas likely to be accidently touched by a user. A removable and cleanable guard can also be used to prevent accidental touching of the dispensing valve.

Accordingly, the invention features an automatic lubricant dispenser that includes a top component having at its front end a dispensing component, the dispensing component including a dispensing valve for dispensing the lubricant, a base for supporting the dispenser on a flat surface, and a middle component connecting the top component to the base, wherein the front portion the top component extends away from the middle of the front portion of the middle component at least 5 cm (e.g., at least 10 or 15 cm). The dispenser might also include a sensor for detecting the proximity of a user's hand to the dispensing valve and thereby activating a signal which causes the dispenser to deliver lubricant through the dispensing valve. The dispenser might also feature a contamination guard located in the front portion of the top component partially surrounding the dispensing valve. The contamination guard can be removable from the dispenser and/or be composed of (e.g., be made of, be coated with, or be impregnated with) an anti-microbial material. In one variation, the front portion of the middle component can include an anti-microbial material.

Although methods and materials similar or equivalent to those described herein can be used in the practice or testing of the present invention, suitable methods and materials are described below. All publications mentioned herein are incorporated by reference in their entirety. In the case of conflict, the present specification, including definitions will control. In addition, the particular embodiments discussed below are illustrative only and not intended to be limiting.

DETAILED DESCRIPTION

The invention encompasses methods, devices, and kits for hygienically dispensing lubricants in a clinical setting. The below described preferred embodiments illustrate adaptation of these methods, devices, and kits. Nonetheless, from the description of these embodiments, other aspects of the invention can be made and/or practiced based on the description provided below.

Dispensing Devices

Figure 1:
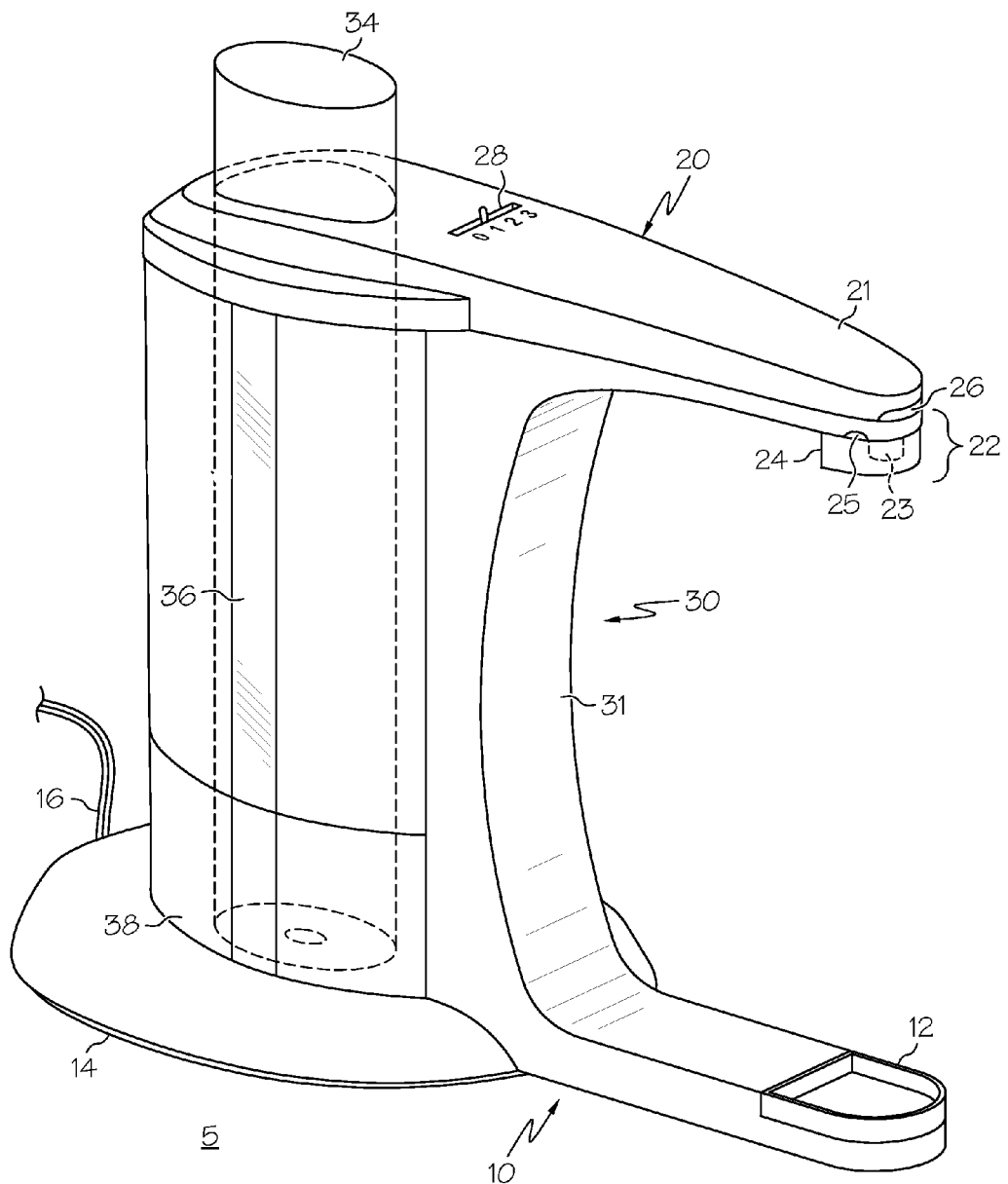
FIG. 1 is a schematic illustration of a lubricant dispensing device of the invention shown with a lubricating gel cartridge installed.

Referring now to FIG. 1, in an exemplary embodiment of the invention, an automatic lubricating gel dispenser 5 includes a base 10, a top component 20, and a middle component 30 connecting the base 10 to the top component 20. The front portion of the top component 20 (and optionally of the base 10 as shown in FIG. 1) extends away from the middle of the front portion 31 of the middle component 30 at least about 5 cm (e.g., at least 5, 6, 7, 8, 9, 10, 11, 12, 13, 14, 15, 16, 17, 18, 19 or 20 cm) to reduce the chance that a user's hand or glove will accidentally touch and possibly contaminate the middle component 30. The front portion of the middle component 30 is shown in FIG. 1 as arcuate, although other arrangements are possible, e.g., straight.

The height of the dispenser 5 should be sufficient so that a user can comfortably place his hand under the front portion 21 of the top component 20, e.g., at least 10 cm, but preferably at least 15 or 20 cm. The height of the middle component 30 should also be sufficient for a user to comfortably place his hand under the front portion 21 of the top component 20 without contacting any part of the dispenser 5, e.g., at least 8 cm, but preferably at least 10, 11, 12, 13, 14, 15, 16, 17, 18, 19, 20 or more cm.

In the embodiment shown in FIG. 1, although other configurations are possible, the base 10 is shaped and sized to securely sit on a flat surface such as a table top. For example, the bottom of base 10 can be substantially planar and made of a high friction material such as synthetic rubber. The base 10 is preferably sufficiently dimensioned to prevent tipping of the dispenser 5, e.g., at least 8, 9, 10, 11, 12, 13, or 14 cm wide by at least 8, 9, 10, 11, 12, 13, or 14 cm long. Optionally, the base 10 can include a device for fastening the dispenser 5 to a flat surface, e.g., a suction cup 14, an adhesive film, a magnet, or a hook and loop type fastener. A drip pan 12 can be included in the front portion of the base 10 to catch any excess lubricant that might drip after being dispensed. Preferably, the drip pan 12 is removable from the base 10 for easy cleaning.

The dispenser 5 can be powered by any suitable means. Generally, the dispenser will be powered by electricity from batteries and/or an external current source. In the latter case, the dispenser 5 would include an electrical power cord 16 which could be located on the base 10 as shown in FIG. 1, or less preferably on the top component 20 or the middle component 30.

The top component 20 can have a spout-like shape and a length of at least 10 cm, but preferably at least 15 or 20 cm so that a user can place his or her hand under the middle component 20 with little chance of accidently contacting the front portion of the middle component 20. The top component 20 can include a dispensing component 22 on the bottom side of its front end as shown in FIG. 1. The dispensing component 22 includes a dispensing valve 23 from which lubricant is dispensed, and optionally, a contamination guard 24 which partially surrounds the dispensing valve 23 (without blocking the delivery of lubricant) and protects it from being accidentally touched and contaminated by a user. The guard preferably extends downward farther (e.g., at least 0.3, 0.5, 0.75, 1, 1.5., or 2 cm) than the outlet on valve 23 to protect the outlet from accidentally being touched by a user. The contamination guard 24 is preferably removable from the dispenser 5 for easy cleaning. It can be made of any suitable material such as a plastic or metal, and can also be composed of an anti-microbial material (e.g., such as silver, an anti-microbial polymer, or an anti-microbial nanocomposite material). In an alternative configuration, rather than using a guard 24 to protect the valve 23, the valve can be recessed (e.g., at least 0.3, 0.5, 0.75, 1, 1.5., or 2 cm) in an opening or bore on the underside of the front portion 21 of the top component 20. In this arrangement, the portions of the top component 20 near the opening or bore could be composed of an anti-microbial material.

To detect the hand of a user and thereby cause the dispenser 5 to dispense lubricant, the dispenser can include a sensor 25 such as an infrared sensor which detects the proximity of the users hand and responds by sending signals to other components (e.g., an electrical pump, conduits, and valves interposed between the lubricant storage component and the valve 23) of the dispenser 5 which cause the lubricant to be dispensed through the valve 23. The sensor 25 can be located on the top component 20 as shown in FIG. 1, but might also be located on the middle component 30 or the base 10. A number of suitable sensors, pumps, and other components of this system are well known in the art.

A refill warning device 26 such as a light or sound generator can also be included on the dispenser 5 to signal to a user that lubricant needs to be added. The dispenser 5 can also include a lubricant volume controller 28 which controls how much lubricant is dispensed per activation. This controller might be a rheostat or could be a switch with set volume levels (e.g., levels 1, 2, and 3). The amount of lubricant dispensed per activation could be between 2-10 ml (e.g., 2, 3, 4, 5, 6, 7, 8, 9, or 10 ml +/−10%).

Figure 2:
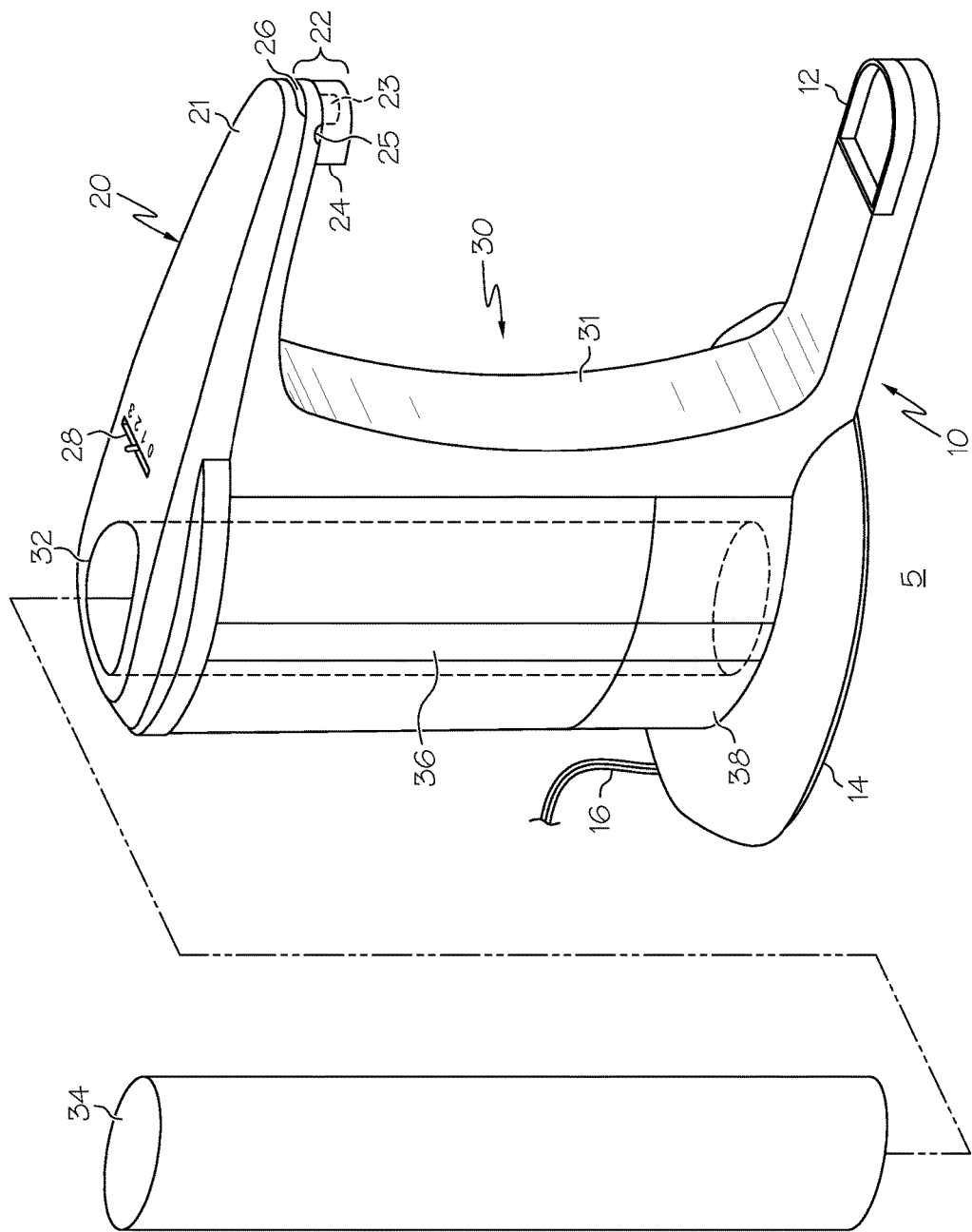
FIG. 2 is a schematic illustration of the lubricating gel cartridge and the lubricant dispensing device of FIG. 1 shown with the lubricating gel cartridge removed.

The middle component 30 can include a reservoir into which lubricant is poured and stored, or preferably as shown in FIGS. 1 and 2, an acceptor 32 for a pre-filled lubricant cartridge 34. The acceptor 32 can be specifically designed to securely hold the cartridge 34 and align it with tubes that communicate with the valve 23 and other components such as a pump. The acceptor 32 might also be designed to puncture a sealing mechanism of the cartridge 34 so that lubricant would only be allowed to flow out of the cartridge 34 once the sealing mechanism was punctured. In the embodiment shown in FIG. 1, a window 36 for showing the level of lubricant runs vertically through the outer wall of the cartridge 34. The middle component 30, and particularly the front portion of this component 30, can include an anti-microbial material (see above) that could help kill any viruses and/or bacteria that might accidentally get on this component.

For patient comfort, the dispenser 5 might also include a heating unit 38 (shown on the bottom portion of the middle component 30 in the embodiment shown in FIG. 1) for warming the lubricant. The heating unit 38 could be an electrical heating unit that can warm the lubricant to greater than 30° C. (e.g., 30, 31, 32, 33, 34, 35, 36, 37, 38, 39, 40 or more ° C.).

As mentioned above, the outer surface of various parts of the dispenser 5 that are most likely to be accidentally contacted by a user's hand can include an anti-microbial material. In addition to this, the surface of the components making up the dispenser can be composed of materials that are resistant to being degraded by commonly used medical disinfectants such as alcohol. These materials might include metals (e.g., stainless steel, copper, and silver) or solvent-resistant plastics.

In operation, a health care provider preparing to apply lubricant to a patient would place a gloved hand under the dispensing component 22 without touching any part of the dispenser. The sensor 25 would detect the gloved hand and send a signal to a pump or like device that would signal the dispenser 5 to move lubricant from the cartridge 34 out through the valve 23. Because the dispenser 5 is never touched by the health care provider, he or she can obtain lubricant without contaminating the dispenser 5 even with a glove that might have a patient's bodily fluid or tissues on it. The elongation of top component 20 greatly reduces the chance that a health care provider will accidently touch the dispenser 5, and the contamination guard 24 prevents a user from accidently touching the dispensing valve 23.

Other Embodiments

It is to be understood that while the invention has been described in conjunction with the detailed description thereof, the foregoing description is intended to illustrate and not limit the scope of the invention, which is defined by the scope of the appended claims. For example, the dispenser might be configured for wall mounting by having a means for securing the dispenser to a wall. Other aspects, advantages, and modifications are within the scope of the following claims.

What is claimed is:

1. An automatic lubricant dispenser comprising:
    an elongated top component having a length of at least 10 cm and comprising at its front end a dispensing component, the dispensing component comprising a dispensing valve for dispensing the lubricant,
    a base for supporting the dispenser on a flat surface, and
    a middle component connecting the top component to the base, wherein the front portion of the top component extends away from the middle of the front portion of the middle component at least 5 cm.

2. The dispenser of claim 1, wherein the front portion of the top component extends away from the middle of the front portion of the middle component at least 10 cm.

3. The dispenser of claim 1, wherein the front portion of the top component extends away from the middle of the front portion of the middle component at least 15 cm.

4. The dispenser of claim 1, further comprising a sensor for detecting the proximity of a user's hand to the dispensing valve and thereby activating a signal which causes the dispenser to deliver lubricant through the dispensing valve.

5. The dispenser of claim 1, further comprising a contamination guard located in the front portion of the top component partially surrounding the dispensing valve.

6. The dispenser of claim 5, wherein the contamination guard is removable from the dispenser.

7. The dispenser of claim 5, wherein the contamination guard comprises an anti-microbial material.

8. The dispenser of claim 1, wherein the front portion of the middle component comprises an anti-microbial material.

9. An automatic lubricant dispenser having a height of at least 15 cm, the dispenser comprising:
    an elongated top component having a length of at least 10 cm and comprising at its front end a dispensing component, the dispensing component comprising a dispensing valve for dispensing the lubricant,
    a base for supporting the dispenser on a flat surface, and
    a middle component connecting the top component to the base, wherein the front portion of the top component extends away from the middle of the front portion of the middle component at least 5 cm and the height of the middle component is at least 15 cm.

10. The dispenser of claim 9, wherein the dispenser further comprises an acceptor for a lubricant cartridge.

11. The dispenser of claim 10, wherein the acceptor comprises a puncture mechanism for puncturing a sealing mechanism of the cartridge.

12. The dispenser of claim 9, wherein the dispenser further comprises a lubricant volume controller for controlling the amount of lubricant dispensed.

13. The dispenser of claim 9, wherein the dispenser further comprises a lubricant storage component.

14. The dispenser of claim 9, further comprising a sensor for detecting the proximity of a user's hand to the dispensing valve and thereby activating a signal which causes the dispenser to deliver lubricant through the dispensing valve, wherein the amount of lubricant dispensed per activation is between 2-10 ml.

15. The dispenser of claim 9, wherein the dispensing valve is recessed in an opening or bore on the underside of the front portion of the top component.

16. The dispenser of claim 9, wherein the dispensing valve comprises an outlet, and the dispenser further comprises a contamination guard located in the front portion of the top component partially surrounding the dispensing valve, wherein the contamination guard extends downward farther than at least 0.3 cm than the outlet of the dispensing valve.

17. The dispenser of claim 9, further comprising a heating unit for warming the lubricant.

18. The dispenser of claim 9, further comprising a refill warning device to signal that lubricant needs to be added.

19. An automatic lubricant dispenser having a height of at least 15 cm, the dispenser comprising:
    an elongated top component having a length of at least 10 cm and comprising at its front end a dispensing component, the dispensing component comprising a dispensing valve for dispensing the lubricant through an outlet;
    a base for supporting the dispenser on a flat surface, wherein the base is at least 8 cm wide by at least 8 cm long;
    a middle component connecting the top component to the base, wherein the front portion of the top component extends away from the middle of the front portion of the middle component at least 5 cm and the height of the middle component is at least 15 cm;
    an acceptor for a lubricant cartridge;
    a sensor for detecting the proximity of a user's hand to the dispensing valve and thereby activating a signal which causes the dispenser to deliver lubricant through the dispensing valve, wherein the amount of lubricant dispensed per activation is between 2-10 ml;
    a lubricant volume controller for controlling the amount of lubricant dispensed; and
    a contamination guard located in the front portion of the top component partially surrounding the dispensing valve, wherein the contamination guard extends downward farther than at least 0.3 cm than the outlet of the dispensing valve.

* * * * *